United States Patent [19]

Ryals et al.

[11] Patent Number: 5,792,904
[45] Date of Patent: Aug. 11, 1998

[54] METHOD FOR BREEDING DISEASE RESISTEANCE INTO PLANTS

[75] Inventors: John A. Ryals, Cary; Scott J. Uknes, Apex, both of N.C.; Terrence Patrick Delaney, Ithaca, N.Y.; Eric R. Ward, Durham; Henry-York Steiner, Raleigh, both of N.C.

[73] Assignee: Novartis Finance Corporation, New York, N.Y.

[21] Appl. No.: 648,949

[22] Filed: May 16, 1996

Related U.S. Application Data

[63] Continuation-in-part of Ser. No. 165,238, Dec. 10, 1993, abandoned, which is a continuation-in-part of Ser. No. 2,285, Jan. 8, 1993, abandoned.

[51] Int. Cl.$^6$ .............................. A01H 1/04; A01H 1/06
[52] U.S. Cl. ...................... 800/200; 800/230; 800/235; 800/DIG. 56; 800/DIG. 15; 47/58; 47/DIG. 1; 536/24.3
[58] Field of Search .................... 800/200, DIG. 56, 800/230, 235, DIG. 15; 47/DIG. 1, 58; 536/24.3

[56] References Cited

FOREIGN PATENT DOCUMENTS

| | | |
|---|---|---|
| 0306139 | 3/1989 | European Pat. Off. . |
| 0317239 | 5/1989 | European Pat. Off. . |
| 0320130 | 6/1989 | European Pat. Off. . |
| 0392225 | 10/1990 | European Pat. Off. . |
| 0440304 | 8/1991 | European Pat. Off. . |
| WO89/07647 | 8/1989 | WIPO . |

OTHER PUBLICATIONS

Tanksley et al. RFLP mapping in plant breeding: new tools for an old science. Biotechnology, vol. 7, 257–264, 1989.

Alexander, D., et al., "Systemic Acquired Resistance in Tobacco: Use of Transgenic Expression to Study the Functions of Pathogenesis–Related Proteins", *Current Plant Science and Biotechnology in Agriculture*, (Advances in Molecular Genetics of Plant–Microbe Interactions vol. 2.) 6th International Symposium on Washington, 14: 527–533 (1992).

Alexander, D., et al., "Increased Tolerance to Two Oomycete Pathogens in Transgenic Tobacco Expressing Pathogenesis–related Protein 1a", *PNAS*, 90: 7327–7331 (1993).

Bol, J.F., et al., "Plant Pathogenesis–related Proteins Induced by Virus Infection", *Annu. Rev. Phytopathol.*, 28: 113–138 (1990).

Crop Science Society of America, In Glossary of Crop Science Terms. p. 18 (1992).

Dangl, J.L., "Applications of *Arbidopsis thaliana* to Outstanding Issued in Plant–Pathogen Interactions", *International Review of Cytology*, 144: 53–83 (1993).

Debener, T., et al., "Identification and Molecular Mapping of a Single *Arabidopsis thaliana* Locus Determining to a Phytopathogenic *Pseudomonas syringae* Isolate", *The Plant Journal*, 1(3): 289–302 (1991).

Delaney, T.P., et al., "A Central Role of Salicylic Acid in Plant Disease Resistance", *Science*, 266: 1247–1250 (1994).

Dietrich, R.A., et al., "Arabidopsis Mutants Simulating Disease Resistance Response", *Cell*, 77: 565–577 (1994).

Evans et al., *Science*, 213: 907–909 (1981).

Gaffney, T., et al., "Requirement of Salicylic Acid for the Induction of Systemic Acquired Resistance", *Science*, 261: 754–756 (1993).

Glascock, C.B., et al., "Transgenic Tobacco Resistant to Phytophthora Parasitica: Analysis of Expression and Activity of a Novel Pathogenesis–related (PR) Protein, SAR 8.2", Abstract Y205, *J. Cell. Biochem. Suppl.*, (Keystone Symposium on Crop Improvement Via Biotechnology, Apr. 10–16, 1992) 16F: 215 (1992).

Helentjairs, T., et al., "Construction of Genetic Linkage Maps in maize and Tomato Using Restriction Fragment Length Polymorphisma", *Theor. Appl. Genet.*, 72: 761–769 (1986).

Huang, H. et al., "An Improved Procedure for Transforming *Arabidopsis thaliana* (*Landsberg erecta*) Root Explant", *Plant Molecular Biology Reporter*, 10(4): 372–383 (1992).

Kuc, Joseph, "Induced Immunity to Plant Disease", *BioScience*, 32(11): 854–860 (1982).

Langford, A.N., "Autogenous Necrosis in Tomatoes Immune from *Cladosporium fulvum* Cooke", *Canadian Journal of Research*, 26(C): 35–64 (1947).

Lawton, K., et al., "The Molecular Biology of Systemic Acquired Resistance", *Proceedings of the 2nd European Federation of Plant Pathology Conference*, pp. 1–13 (1992).

Lawton, K., et al., "The Molecular Biology of Systemic Acquired Resistance", *Developments in Plant Pathology* (Mechanisms of Plant Defense Responses), 2nd Int'l Conference of the European Foundation for Plant Pathology, Strasbourg, France, Aug. 24–27, 1992, 2: 422–432 (1993).

Linthorst, H.J.M., et al., "Analysis of Acidic and Basic Chitinases From Tobacco and Petunia and Their Constitutive Expression in Transgenic Tobacco", *Molecular Plact–Microbe Interactions*, 3(4): 252–258 (1990).

(List continued on next page.)

*Primary Examiner*—Douglas W. Robinson
*Assistant Examiner*—Melissa L. Kimball
*Attorney, Agent, or Firm*—J. Timothy Meigs

[57] ABSTRACT

Methods are provided for selecting parental plants having disease resistance and for using these plants in breeding programs. In one method of the invention, lesion mimic mutants are screened for either resistance to a pathogen of interest or for the expression of systemic acquired resistance (SAR) genes. Such mutants having the desired traits or expressing the desired genes are then used in breeding programs. Parent plants can also be selected based on the constitutive expression of SAR genes. These mutants are phenotypically normal yet exhibit a significant level of disease resistance. Also disclosed are plant mutants that do not express systemic acquired resistance genes even when induced by a pathogen and methods of use for such mutants.

19 Claims, 13 Drawing Sheets

OTHER PUBLICATIONS

Michelmore, R.W., et al., "Identification of Markers Linked to Disease–resistance Genes by Bulked Segregant Analysis: A Rapid Method to Detect Markers in Specific Genomic Regions by Using Segregating Populations", *Proc. Natl. Acad. Sci.*, 88: 9828–9832 (1991).

Moffat, *Science*, 258: 1580–1581 (1992).

Neuffer, M.G., et al., "Dominant Disease Lesion Mmiics in Maize", *The Journal of Heridity*, 66: 265–270 (1975).

Neuffer, M.G., et al. "Gene Structure and Function in Higher Plants", *Proceedings of the Int'l Symposium held at Hyderabad, India, Dec. 7–9, 1983*. G.M. Reedy and E.H. Coe, Jr., (Eds) Oxxford & IBH Publishing Co., 124–134 (1983).

Reuveni R., et al., Abstract #A1104, "Systemic Resistance Against Northern Leaf Blight and Common Rust in Maize Induced by Foliar Spray of Phosphates", *Phytopath*, 82(10): 1179 (1992).

Ross, A.F., "Localized Acquired Resistance to Plant Virus Infection Hypersensitive Hosts", *Virology*, 14: 329–339 (1961).

Ross, A.F., "Systemic Acquired Resistance Induced by Localized Virus Infections in Plants", *Virology*, 14: 340–358 (1961).

Ross, A.F. "Systemic Effects of Local Lesion Formation", in *Viruses of Plants*, A.B.R. Beemster and J. Dijkstra, eds (Amsterdam: North–Holland), pp. 127–150 (1966).

Ryals, J., et al., "The Molecular Biology of Systemic Acquired Resistance", Abstract Y008, *J. Cell. Biochem. Suppl.*, (Keystone Sumposium on Crop Improvement Via Biotechnology, Apr. 10–16, 1992), 16F: 200(1992).

Simmonds, In Principles of Crop Improvement, Longman, London pp. 274–276 (1979).

Uknes, S., et al., "Acquired Resistance in Arabidopsis", *The Plant Cell*, 4: 645–656 (1992).

Uknes, S., et al., "Biological Induction of Systemic Acquired Resistance in Arabidopsis", *MPMI*, 6(6): 692–398 (1993).

Walbot, V., et al., "Disease Lesion Mimic Mutations", *Genetic Engineering of Plants*, Tsuno Kosug, Carole P. Meredith and Alexander Hollaender (eds), Plenum Publishing Corp., pp. 431–442 (1983).

Ward, E.R., et al., "Coordinate Gene Activity in Response to Agents that Induce Systemic Acquired Resistance", *The Plant Cell*, 3: 1085–1094 (1991).

Weyman, K., et al., "Suppression and Restoration of Lesion Formation in Arabidopsis lsd Mutants", *The Plant Cell*, 7: 2013–2022 (1995).

METHOD FOR BREEDING DISEASE RESISTEANCE INTO PLANTS

This Application is a Continuation-in-Part Application of U.S. application Ser. No. 08/165,238, filed Dec. 10, 1993, now abandoned, herein incorporated by reference, which was a Continuation-in-Part Application of U.S. application Ser. No. 08/002,285, filed Jan. 8, 1993, now abandoned, herein incorporated by reference.

FIELD OF THE INVENTION

The present invention relates to disease resistance in plants, particularly identifying and breeding disease resistance into plants.

BACKGROUND OF THE INVENTION

Diseases are particularly destructive processes resulting from specific causes and characterized by specific symptoms. Usually, the disease causes damage to the host organism, the local population, or the entire species. Generally the symptoms can be related to a specific cause, usually a pathogenic organism. In plants, a variety of pathogenic organisms cause a wide variety of diseases or disease symptoms.

The severity of the destructive process depends on the aggressiveness of the pathogen and the response of the host. One objective of many breeding programs is to increase the resistance of the host plant to disease.

In many plant species, an initial inoculation by a necrotizing pathogen can immunize the plant to subsequent infection. This acquired disease resistance was first documented in 1901 and is thought to play an important role in the preservation of plants in nature. Particularly well characterized examples of plant immunity are the phenomenon of systemic acquired resistance (SAR) in tobacco and induced resistance in cucumber. In these systems, inoculation by a necrotizing pathogen results in systemic protection against subsequent infections by that pathogen as well as a number of other agronomically important bacterial, fungal and viral pathogens.

The SAR response can be divided conceptually into two phases. The initiation phase begins when a pathogen elicits tissue necrosis and causes the release of a systemic signal. That signal translocates throughout the plant, is perceived in target tissues and transduced through gene expression to resistance. The maintenance phase refers to the quasi steady-state during which resistance is manifested.

Immunization compounds are chemicals that induce the immunity response in plants. Such compounds can be of natural origin, such as salicylic acid , or can be synthetic chemicals, such as 2,6-dichloroisonicotinic acid. Treatment with a pathogen or an immunization compound induces the expression of least nine sets of genes in tobacco, the best characterized species. Different numbers and types of genes can be expressed in other plants. The levels of induction for SAR-related genes induced by immunization compounds are as high as 10,000-fold over background.

There has been some effort to clone the genes involved in SAR. These genes could then be used to genetically engineer plants for immunity against pathogens.

While there is excitement over advances in plant genetic engineering, the prospects for the general use of these techniques for plant improvement are tempered by the realization that very few genes corresponding to plant traits of interest have been identified or cloned. Further, traits of interest often involve multi-gene families.

Selection for plants carrying pathogen or disease resistance genes is thus laborious and time consuming. There is therefore needed a method to identify plants carrying useful resistance genes for use in plant breeding programs.

SUMMARY OF THE INVENTION

The present invention is drawn to methods for breeding disease resistance or resistance to pathogens into plants. Lesion or disease mimic mutants are utilized to identify plants having desired traits. The method involves selecting disease lesion mimic mutants based on either resistance to a pathogen of interest or on the expression of systemic acquired resistance (SAR) genes. Such mutants having the desired traits or expressing the desired genes are then used in breeding programs.

Alternatively, plants for use in a breeding program can be selected based on constitutive expression of SAR genes. That is, visible phenotype normal plants that constitutively express SAR genes can be utilized. Progeny are screened for either resistance to a pathogen of interest or for the expression of systemic acquired resistance genes. Because these mutants have a significant level of disease resistance and no apparent negative phenotype, they have utility in breeding crop plants with constitutive, hereditary disease resistance.

The invention is further drawn to the selection and utilization of plant mutants which do not express systemic acquired resistance genes, even when induced by a pathogen. Such mutants have utility in disease and pathogenesis testing and fungicide screening programs.

DETAILED DESCRIPTION OF THE INVENTION

Figure 1:
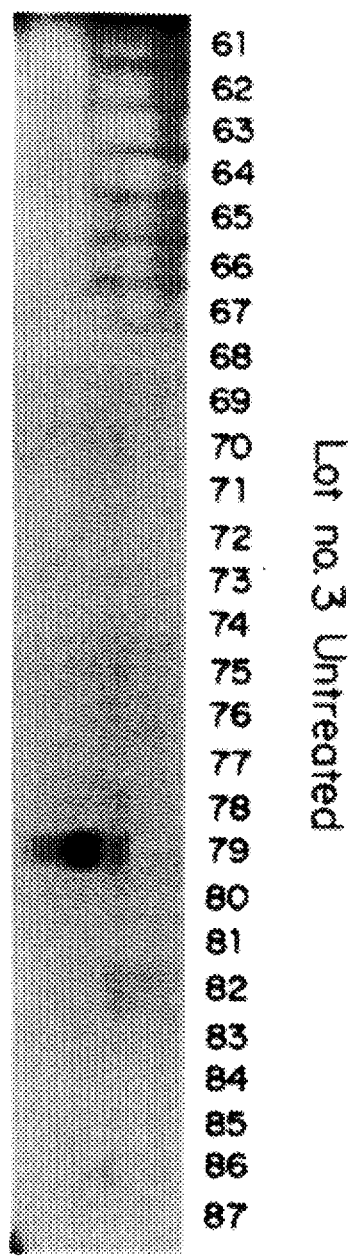
FIG. 1. The isolation of a single mutant Arabidopsis plant that constitutively expresses an SAR gene. RNA was isolated from various individual mutant plants as described elsewhere. RNA gel blot analysis was conducted using the Arabidopsis PR-1 gene as a probe. A single plant (79#) out of 27 shows high level expression of PR-1.

Methods for breeding disease resistance into plants are provided. Particularly, in one embodiment the lesion mimic phenotype is used as a tool to identify plants having genes of interest for a breeding program.

Lesion mimic mutants are widely known in plants. Such lesion mimic mutants may be obtained from mutagenesis or by spontaneous mutation. In fact, both spontaneous and mutagen-induced cases of dominant and recessive mutants causing discrete leaf lesion formation have been reported in a number of plants including maize, tomato, wheat, tobacco, barley, sunflower, cucumber, etc. See, for example, Neuffer and Calvert (1975) The Journal of Heredity 66:265–270; Cameron J. W. (1964) Maize Genet. Coop. News Letter 38:32–33; Gardner C.O. (1971) Maize Genet. Coop. News Letter 45:150; Hornbrook and Gardner (1970) Rad. Botany 10:113–117; Simmonds N. W. (1950) Maize Genet. Coop. News Letter 24:26–27; and Walbot et al. (1983) in *Genetic Engineering of Plants*, Kosuge et al. (eds.) Plenum Publishing Corporation, 1983.

The present invention is the first to recognize that the lesion mimic phenotype is associated with SAR and the expression of pathogenesis-related proteins and that the expression of SAR genes can be separated from the lesion phenotype. Thus, the lesion phenotype can be utilized to select for plants expressing SAR genes. The expression of these genes could be of substantial importance in a breeding program as an added resistance factor.

Pathogenesis-related proteins (PR proteins) are plant proteins induced following infection by a pathogen. Some of these proteins have a role in providing systemic acquired resistance to the plant. These plant proteins are induced in large amounts in response to infection by various pathogens, including viruses, bacteria and fungi. Pathogenesis-related (PR) proteins were first discovered in tobacco plants (*Nicotiana tabacum*) reacting hypersensitively to infection with tobacco mosaic virus (TMV). Subsequently, PR proteins have been found in many plant species (See Redolfi et al. (1983) Neth J Plant Pathol 89:245–254; Van Loon (1985) Plant Mol. Viol. 4:111–116; and Uknes et al. (1992) Plant Cell 4:645–656.) Such proteins are believed to be a common defensive systemic response of plants to infection by pathogens.

Pathogenesis-related proteins include but are not limited to SAR8.2a and SAR8.2b proteins, the acidic and basic forms of tobacco PR-1a, PR-1b, and PR-1c, PR-1', PR-2, PR-2', PR-2", PR-N, PR-O, PR-O', PR-4, PR-P, PR-Q, PR-S, and PR-R major proteins, cucumber peroxidases, basic cucumber peroxidase, the chitinase which is a basic counterpart of PR-P or PR-Q, and the beta-1,3-glucanase (glucan endo- 1,3-beta-glucosidase, EC 3.2.1.39) which is a basic counterpart of PR-2, PR-N or PR-O, and the pathogen-inducible chitinase from cucumber. See, for example, Uknes et al. (1992) The Plant Cell 4:645–656 and the references cited therein, as well as U.S. application ser. No. 848,506, filed Mar. 6,1992, herein incorporated by reference.

SAR or SAR-like genes are expressed in all plant species exhibiting systemic acquired resistance. Expression of such genes can be determined by probing with known SAR DNA sequences. For example, see, Lawton et al. (1992) Proceedings of the Second European Federation of Plant Pathology (1983), In: Mechnisms of Defence Responses in Plants, B. Fritig and M. Legrand (eds), Kluwer Academic Publishers, Dordrecht, pp. 410–420; Uknes et al. (1992) The Plant Cell 4:645–656; and Ward et al. (1991) The Plant Cell 3:1085–1094. Methods for hybridization and cloning are well known in the art. See, for example, *Molecular Cloning, A Laboratory Manual*, 2nd Edition, Vol. 1–3, Sambrook et al. (eds.) Cold Spring Harbor Laboratory Press (1989) and the references cited therein.

Alternatively such SAR or SAR-like genes can be found by other methods such as protein screening, +/−screening, etc. See, for example, U.S. application Ser. No. 848,506 filed Mar. 6,1992; Liang and Pardee (1992) Science 257:967–971; and St. John and Davis (1979) Cell 16:443; herein incorporated by reference.

The present invention recognizes that SAR genes are constitutively expressed in some lesion mimic mutants in plants. Furthermore, the lesion mimic phenotype can be separated from expression of the SAR genes. Therefore, lesion mimic mutants expressing SAR genes can be utilized in breeding programs. Progeny can be selected based on expression of the SAR genes or resistance to pathogens and a desired phenotype. This method offers an additional source of resistance to pathogens for use in breeding programs.

The present invention further recognizes that SAR genes may be constitutively expressed in plants which do not exhibit any lesion formation or necrosis. That is, the plants display a normal phenotype. Such plants can also be used in breeding programs. To identify and select phenotypically normal plants which constitutively express SAR genes, northern analysis is performed to detect expression of SAR genes. Known SAR DNA sequences can be utilized in cross-hybridization experiments as described in Uknes et al. (1992) The Plant Cell 4:645–656. Methods for the hybridization and cloning of nucleic acid sequences are well known in the art. (See, Molecular Cloning, A Laboratory Manual, 2nd Edition, Vol. 1–3, Sambrook et al. (eds.) Cold Spring Harbor Laboratory Press (1989) and the references cited therein.)

Once plants which constitutively express SAR genes are selected they can be utilized in breeding programs to incorporate constitutive expression of the SAR genes and resistance to pathogens into plant lines. Progeny for further crossing are selected based on expression of the SAR genes and disease resistance as well as for other characteristics important for production and quality.

Pathogens of the invention include but are not limited to viruses or viroids, e.g. tobacco or cucumber mosaic virus, ringspot virus or necrosis virus, pelargonium leaf curl virus, red clover mottle virus, tomato bushy stunt virus, and like viruses; fungi, e.g. *Phythophthora parasitica, Peronospora tabacina*, etc.; bacteria, e.g. *Pseudomonas syringae, Pseudomonas tabaci*, etc.; insects, such as aphids e.g. *Myzus persicae*; nematodes, e.g. *Meloidogyne incognita*; lepidoptera, e.g. *Heliothus spp.* etc. The methods of the invention are useful against a number of disease organisms of maize including but not limited to downy mildews such as *Scleropthora macrospora, Sclerophthora rayissiae, Sclerospora graminicola, Peronosclerospora sorphi, Peronosclerospora philippinensis, Peronosclerospora sacchari, Peronosclerospora maydis*; rusts such as *Puccinia sorphi, Puccinia polysora, Physopella zeae*; other fungi such as *Cercospora zeae-maydis, Colletotrichum graminicola, Fusarium monoliforme, Exserohilum turcicum, Bipolaris maydis*; and bacteria such as *Erwinia stewartii*.

The present invention avoids the screening of a large amount of material, including world collections and related species, generally necessary to identify usable resistance genes. Instead the lesion mimic phenotype is used to identify plants which potentially express resistance genes.

Accordingly, lesion mimic mutants of a plant of interest are selected and tested for resistance to a pathogen of interest or alternatively for constitutive expression of SAR genes. Such mutants are then used in breeding programs to introduce the resistance trait into breeding lines. That is, the constitutive expression of the SAR genes is introduced into plants. Such constitutive expression of the SAR genes is associated with immunity to pathogens.

Following the use of the selected lesion mutant or plant which constitutively expresses SAR genes in the breeding program, the resistance trait is incorporated into plant lines through breeding in combination with other characteristics important for production and quality. Breeding approaches and techniques are known in the art. See, for example, Welsh J. R., *Fundamentals of Plant Genetics and Breeding*, John Wiley & Sons, N.Y. (1981); *Crop Breeding*, Wood D. R. (Ed.) American Society of Agronomy Madison, Wisconsin (1983); Mayo O., *The Theory of Plant Breeding*, Second Edition, Clarendon Press, Oxford (1987); Singh, D. P., *Breeding for Resistance to Diseases and Insect Pests*, Springer-Verlag, N.Y. (1986); and Wricke and Weber, *Quantitative Genetics and Selection in Plant Breeding*, Walter de Gruyter and Co., Berlin (1986).

Lesions are a hypersensitive reaction characterized by a local necrosis of the tissues immediately surrounding the infection site of the pathogen and a subsequent localization of the pathogen, which is in contrast to a sensitive reaction wherein the pathogen spreads throughout the plant. Lesion mimic mutants exhibit the hypersensitive reaction without having had any contact with a pathogen.

Disease lesion mimics have been reported in a variety of plants including but not limited to maize, tomato, wheat, arabidopsis, oats, tobacco, sunflower, cucumber, etc. Accordingly, the invention can be used in breeding any plant in which lesion mimic mutants can be found or induced through mutagenesis. Methods are known in the art for mutagenesis and selection.

After lesion mimic mutants or phenotypically normal plants expressing SAR genes have been identified, further analysis can be performed which yield information which is useful in breeding programs. For example, restriction fragment length polymorphisms (RFLP) associated with the expression of the SAR genes and resistance can be identified. Once at least one RFLP associated with the disease resistance is determined, this RFLP can then be used to screen for the presence of the resistance phenotype. RFLPs are valuable to plant breeders to identify genes affecting agronomic traits on the plant genome through the identification of linked genetic markers. Genetic linkage analysis between DNA polymorphisms and traits of agronomic importance is useful to identify agronomically important genes, to classify inbreds, hybrids and breeding populations according to their genes, and then more effectively incorporate these genes into improved inbreds and hybrids.

RFLPs associated with disease resistance would be of great value to breeders. Therefore, the invention encompasses analyzing chromosomes to identify DNA polymorphisms linked with the lesion mimic phenotype and with expression of SAR genes.

To practice the invention, the lesion mutant phenotype is first used as the phenotype associated with disease resistance. RFLPs can then be found which are associated with the lesion phenotype and disease resistance. The RFLP can then be used in the breeding program. The identified genetic linkages between specific probes and genetic components of agronomically important traits are used as an aid in selecting plants and populations in "classical" plant breeding based on Mendelian genetics.

Methods for determining RFLPs and the identification of polymorphisms associated with particular traits are known in the art. See, for example, Burr et al. (1983), "The application of restriction fragment length polymorphism to plant breeding", In *Genetic engineering principles and methods*, Vol. 5 (eds J. D. Selow & A. Hollaender) pp. 45–59, New York, Plenum Press; Helentjaris T. (1987) Trends in Genetics 3:217–221; Helentjaris et al. (1985) Plant Mol. Biol. 5:109–118; International application WO89/07647; European patent application publication No. 0317239; and European patent application publication number 0306139.

In a typical method to identify a polymorphism according to the invention, DNA is extracted from the plant cell and digested with a given restriction endonuclease. After the digest is obtained, and the digested DNA is separated by standard techniques such as agarose gel electrophoresis, the separated bands are probed with a DNA fragment coding for the RFLP sequence.

Probes must be found to detect a polymorphism if it is to be useful for testing linkage to the desired trait. The polymorphism must be found to be linked to genes affecting traits or to other useful markers in studies, or to be immediately adjacent to pre-existing markers. The particular probe can be of any desired sequence length as long as it is capable of identifying the polymorphism in the involved DNA region or locus.

Methods for generating additional new DNA fragments also linked with the gene for a particular trait are as follows. A first method is to test randomly chosen DNA fragments that map to the appropriate region of the genomic map. Such mapping can be achieved by in situ hybridization to metaphase chromosome spreads or by genet mapped to the region.

Additional DNA probes may be obtained by constructing a library from DNA isolated from metaphase chromosomes. Such chromosomes may be sorted, for example on a fluorescence activated sorter.

Finally, new DNA probes may be obtained from the region of the chromosome containing the agronomically important gene by using any probes already mapped to the region to "fish out" adjacent overlapping pieces of DNA from genomic libraries (chromosome walking).

Other methods for the identification of markers linked to disease-resistance genes are known in the art and can be used in the present invention. Such methods include, but are not limited to segregant analysis as a method for rapidly identifying markers (Michelmore et al. (1991) Proc. Matl. Acad. Sci. USA 88:9828–9832, herein incorporated by reference), and the use of RAPD (ramdom amplified polymorphic DNAs) as described by Williams et al. (1990) Nucleic Acids Res. 18:6531–6535, herein incorporated by reference.

Methods for labeling the DNA probes and for hybridization are known in the art. See, for example, Sambrook et al., supra.

The present invention further relates to mutants which are defective in their normal response to pathogen infection in that they do not express genes associated with systemic acquired resistance. These mutants are referred to as nim mutants (for non-inducible immunity) and are useful as "universal disease susceptible" (UDS) plants by virtue of their being susceptible to many strains and pathotypes of pathogens of the host plant and also to pathogens which do not normally infect the host plant, but which infect other hosts. They can be selected by treating seeds or other biological material with mutagenic agents and then selecting progeny plants for the UDS phenotype by treating progeny plants with known chemical inducers (e.g. INA) of the systemic acquired response and then infecting the plants with a known pathogen. Non-inducible mutants develop severe disease symptoms under these circumstances, whereas non-mutants are induced by the chemical compound to systemic acquired resistance. nim mutants can be equally selected from mutant populations generated by chemical and irradiation mutagenesis, as well as from populations generated by T-DNA insertion and transposon-induced mutagenesis. Techniques of generating mutant plant lines are well known in the art.

nim mutants provide useful indicators of the evaluation of disease pressure in field pathogenesis tests where the natural resistance phenotype of so-called wild-type (i.e. non-mutant) plants may vary and therefore not provide a reliable standard of susceptibility. Furthermore, nim plants have additional utility for the the testing of candidate disease resistance transgenes. Using a nim stock line as a recipient for transgenes, the contribution of the transgene to disease resistance is directly assessable over a base level of susceptibility. Furthermore, the nim plants are useful as a tool in the understanding of plant-pathogen interactions. nim host plants do not mount a systemic response to pathogen attack, and the unabated development of the pathogen is an ideal system in which to study its biological interaction with the host.

As nim host plants may also be susceptible to pathogens outside of the host-range they normally fall, these plants also have significant utility in the molecular, genetic, and biological study of host-pathogen interactions. Furthermore, the UDS phenotype of nim plants also renders them of utility for fungicide screening. nim mutants selected in a particular host have considerable utility for the screening of fungicides using that host and pathogens of the host. The advantage lies in the UDS phenoytpe of the mutant which circumvents the problems encountered by hosts being differentially susceptible to different pathogens and pathotypes, or even resistant to some pathogens or pathotypes.

nim mutants have further utility for the screening of fungicides against a range of pathogens and pathotypes using a heterologous host i.e. a host which may not normally be within the host species range of a particular pathogen. Thus, the susceptibility of nim mutants of Arabidopsis (which is an easily manipulable species and has limited space requirements) to pathogens of other species (e.g. crop plant species) would facilitate efficacious fungicide screening procedures for compounds against important pathogens of crop plants.

The following examples are offered by way of illustration and not by way of limitation.

EXPERIMENTAL

A. Arabidopsis Lesion Mimic Mutants

Figure 2:
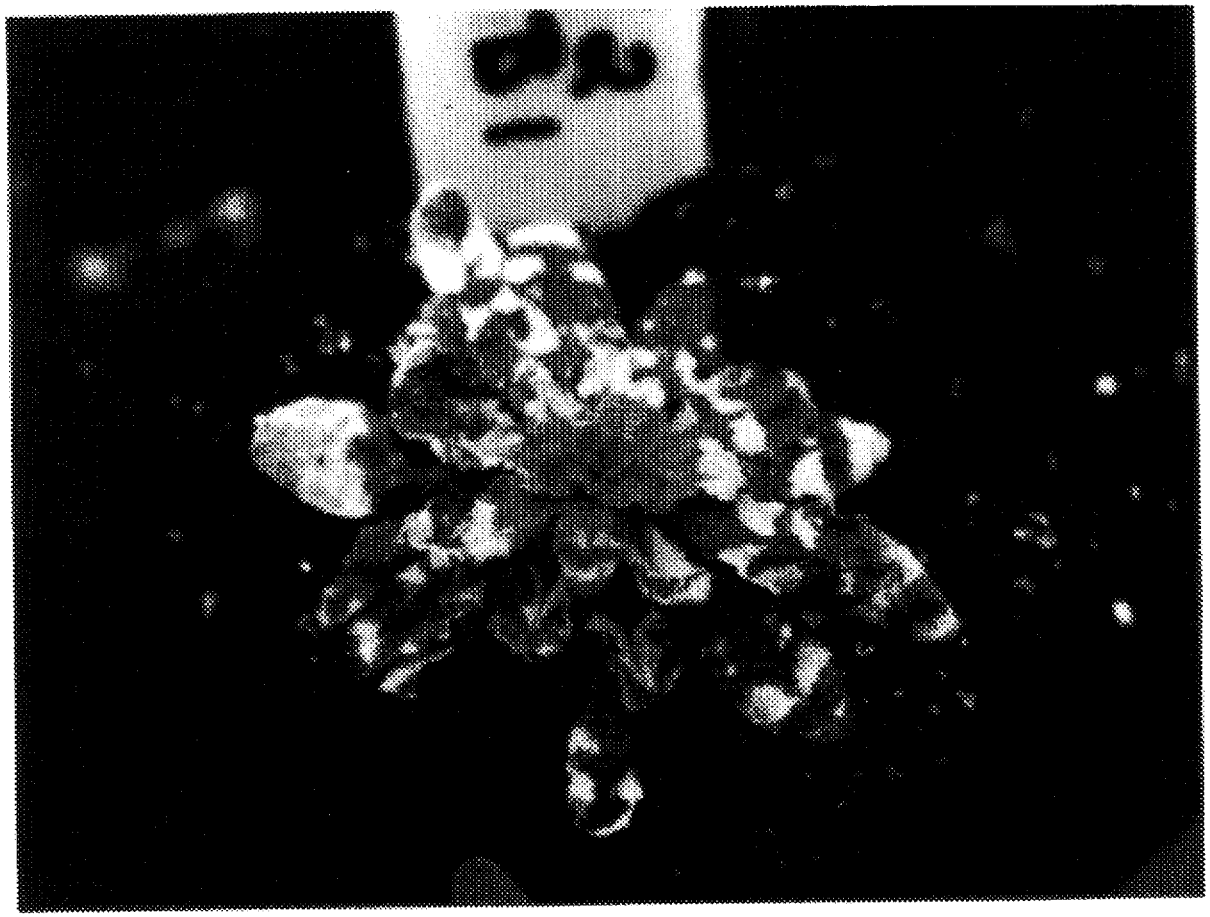
FIG. 2. The Arabidopsis lesion mimic, cim1.

The lesion mimic was isolated during a screen for mutants of Arabidopsis with altered expression of a set of genes associated with the induced resistance phenomenon called systemic acquired resistance (SAR). Specifically, we grew M2, ethyl methane sulfonate (EMS) treated plants in individually marked containers. When the plants were three weeks old one to two leaves were harvested from each plant. RNA was isolated from the leaf samples and analyzed using RNA gel blots probed with pathogenesis related (PR)-1 and PR-2 cDNAs (SAR genes) (FIG. 1). Seed was isolated from plants that showed high level expression of these two RNAs. In addition, any interesting morphological phenotypes were noted. One plant showed lesion-like symptoms on the leaf margins that expanded inward to the midrib of the oldest leaves (FIG. 2). These lesions are first observable when the plant is approximately three weeks old when grown under 9 hour days. The gene conferring the trait which was mutated to give the phenotype was designated cim 1 (cim= Constitutive IMmunity). When progeny from this original plant are grown, approximately half have the lesion-mimic phenotype and high level SAR gene expression. The remainder of the plants look phenotypically normal and have low-background levels of SAR gene expression. These results are consistent with the mutant cim 1 gene having a dominant effect causing both the lesion mimic phenotype and altered gene expression and the original cim1 plant being heterozygous.

The cim1 mutant was tested for susceptibility/resistance to infection by Pseudomonas and Peronospora. For the bacterial pathogen Pseudomonas, in planta bacterial growth was monitored over a five day period after inoculation by injection of $10^5$ colony forming units per ml. using the procedure described by Debener et al. (1991) Plant J 1:289–302. Typically the cim1 mutant line resulted in a reduction in growth by an order of magnitude compared to wild-type. This indicated that the cim1 line had enhanced resistance to infection by Pseudomonas. To assess susceptibility/resistance of cim1 to the fungal pathogen *Peronospora parasitica*, 4 week old plants were either leaf inoculated using 2 ml of a suspension of fresh conidiospores in water (@ $10^5$ spores/ml) or sprayed over the entire aerial plant surface (@ $10^6$ spores/mi). The spore suspension was prepared as described by Dangl et al. (1993) Int Rev Cytol 144: 53–83.

On comparison to wild-type, cim1 plants showed much less hyphal growth and conidiospore production. The leaf surfaces were visibly clearer of Peronospora mycelium than wild-type plants and the plants thus showed elevated resistance to the fungus. The table below shows a summary of data. The altered fungal morphology and resistance phenotype was similar to that shown in Arabidopsis plants pretreated with the SAR-inducing chemical INA (Uknes et al. (1992) Plant Cell 4: 645–656).

TABLE I

*Peronospora parasitica* Disease Ratings

| Plant Line | Number of Plants Expressing Disease Levels[a] | | | | | | total # of plants |
|---|---|---|---|---|---|---|---|
| | 0 | + | ++ | +++ | ++++ | +++++ | |
| Wild type | 0 | 0 | 0 | 0 | 0 | 20 | 20 |
| cim1 | 0 | 6 | 7 | 0 | 0 | 0 | 13 |

[a]This scale is defined as: 0: No conidiophores on plant; +: At least 1 leaf with 1–5 conidiophores; ++: At least one leaf with 5–20 conidiophores; +++: Many leaves with 5–20 conidiophores; ++++: All inoculated leaves with >5 conidiophores; +++++: All inoculated leaves with >20 conidiophores.

In addition to the lesion mimic (cim1), other mutants with high levels of constitutive SAR gene expression were found. Several of these mutants (cim2, cim3 and others) have very high levels of expression with no obvious phenotype. These cim mutants fall into three different classes; Class I, Class II, and Class III (Table II). Class I mutants are characterized by having lesions, high constitutive salicylic acid levels (an endogenous signal for SAR), and high constitutive levels of SAR gene expression. Class II mutants are the same as Class I without the lesion mimic phenotype. Class III mutants have increased levels of SAR gene expression without increased levels of SA or the lesion mimic phenotype.

TABLE II

Arabidopsis mutant types

| ATTRIBUTE | cim Class I | cim Class II | cim Class III |
|---|---|---|---|
| Lesion[1] | + | – | – |
| SA[2] | + | + | – |
| SAR Gene Expression[3] | + | + | + |

[1]The presence +, or absence –, of the Lesion Mimic pheotype
[2]Salicylic Acid detected
[3]As measured by RNA gel blot analysis The EMS treatment was conducted as follows; *Arabidopsis thaliana* ecotype Columbia seed was placed in a solution of EMS for 12–24 hours, the seed was then washed and planted. When the plants were mature, groups of 1000 plants were harvested and the seed was kept in a separately numbered lot. These seeds were the M2 seeds which were planted. EMS-treated seed can be purchased from Lehle seed, Tucson, Ariz.

B. Tobacco Lesion Mimic Mutant

Figure 3:
FIG. 3. A leaf from the tobacco lesion mimic, 1791c-18-2.
Figure 4:
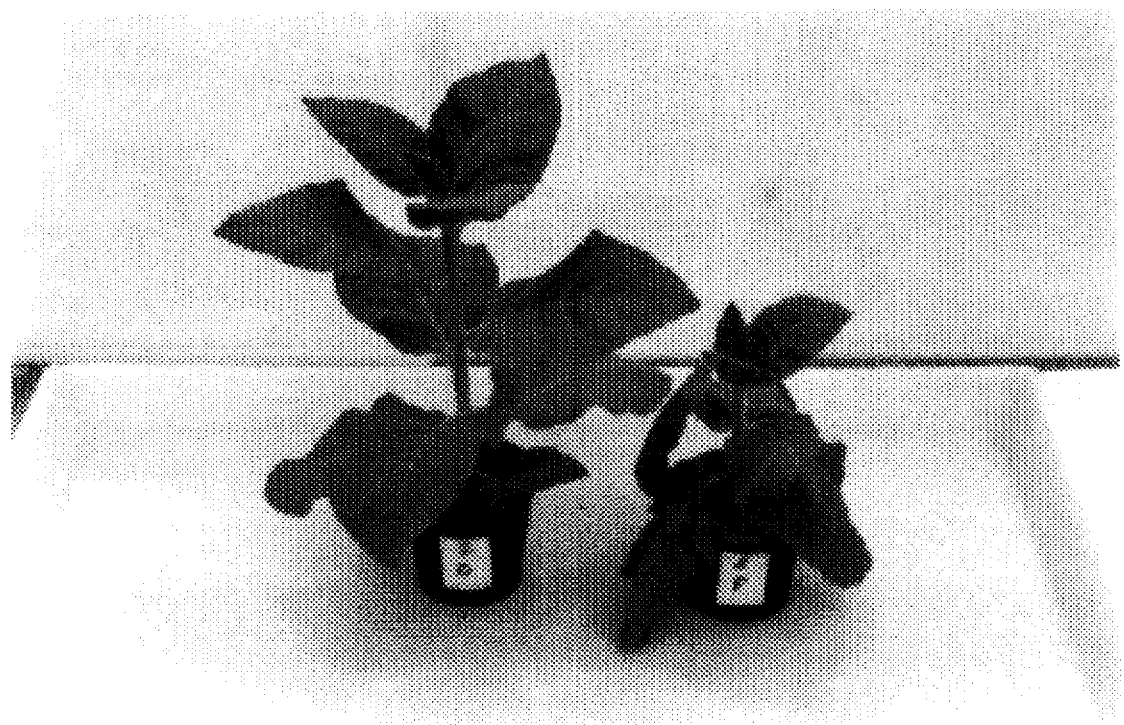
FIG. 4. The tobacco lesion mimic is resistant to *Phytophthora parasitica*. When the plants were approximately 5 weeks old they were infected with *Phytophthora parasitica* by soil application. The photo was taken approximately one week after inoculation. The plant on the left is the lesion mimic and the plant on the right is the control (xanthi-nc tobacco).

One transgenic tobacco line named 1791C-18-2, that was transformed with pathogenesis related protein Q, showed a lesion mimic phenotype (FIG. 3). Fully expanded leaves had many, 1 1–20 millimeter necrotic lesions. These lesions were typically light-brown at the center and surrounded by darkened tissue. When this line was tested, resistance to *Phytophthora parasitica* was observed (FIG. 4). However, other plants lines transgenic for PR-Q but not having the lesion mimic phenotype were not resistant to *Phytophthora parasitica*. This indicated that the observed resistance is caused by the altered phenotype of the plant (lesion mimic) and not the presence of the transgene.

C. Construction And Characterization Of The Transgenic Line 1791C-18-2, Constitutively Expressing PR-O 1. Preparation of Purified PR-Q (For general methods see U.S. Ser. No. 848,506, herein incorporated by reference.)

Plants of *Nicotiana tabacum* cv. Xanthi.nc were grown in a greenhouse and infected when 8 weeks old by rubbing the leaves with a suspension of the common strain (U1) of tobacco mosaic virus at a concentration of 0.5 micrograms/ml, in a solution of 10 mM sodium phosphate (pH 7.0) containing carborundum. Leaves were harvested 7 days later. The intercellular-fluid fraction was made from the leaves by the vacuum infiltration method of Parent and Asselin, (1984) Can. J. Bot. 62:564–569. The proteins PR-P and PR-Q were separated from the other proteins present in the fraction by sequential purification through an Ultragel AcA54 column, a DEAE-Sephacel column, and a reverse-phase HPLC phenyl column, and their recovery was monitored by comparing samples of crude intercellular-fluid with the purified fraction on 10% nondenaturing gels as described by Gianninazzi and Kassanis, (1974) J. Gen. Vir. 23:1–9. Pure PR-Q was obtained from the mixture of PR-Q and PR-P by chromatography on a Brownlee Labs AX-300 HPLC ion-exchange column, using a gradient of 10–250 mM ammonium acetate (pH 7.0).

2. Amino Acid Sequence of PR-Q

Cyanogen bromide and tryptic peptides were made and purified by methods well known in the art, and subjected to automated Edman degradation and analysis.

3. Isolation and Cloning of PR-Q cDNA

Tobacco leaves were infected as described and harvested 5 days later. RNA was prepared by the method of Lagrimini et al. (1987) PNAS 84:7542–7546, cDNA was made from it by the method of Gubler and Hoffman, (1983) Gene 25: 263–269, and the cDNA was cloned into the Eco RI site of the lambdaOngC phage vector available from Stratagene. The library was plated and duplicate filter replicas made. The filters were probed with DNA encoding the tobacco basic chitinase Shinshi et al. (1987) PNAS 84:89–93 under the following conditions: 125 MM NaCl/ 1% SDS/40 mM sodium phosphate, pH 7.2/1 mM EDTA at 50 degrees Celsius; washing was done under the same conditions. Positive plaques were identified and isolated. The isolated phage were plated again, and new duplicate sets of filters made. The tobacco basic chitinase was again used as a probe, but this time the hybridization and washing were done in the previously described solution at 65 degrees Celsius. Plaques which hybridized to the probe at 50 degrees Celsius, but either did not or hybridized weakly at 65degrees Celsius were purified. DNA was isolated from the purified phage, and the cDNA removed by digesting with Eco RI. The Eco RI fragment representing the cDNA was subcloned into the plasmid vector Bluescript, and its sequence determined by dideoxy sequencing using the procedure for double-stranded templates. The identification of the clones as PR-Q was accomplished by comparing the predicted amino acid sequence derived from the cDNA with the amino acid sequence determined from the purified protein.

4. Engineering PR-Q DNA Into Plant Expression/Transformation Vectors

The full-length PR-Q cDNA was inserted into the Eco RI site of the plasmid pCGN1761, which placed it between a duplicated 35S RNA promoter derived from the cauliflower mosaic virus and transcription termination signals encoded by the 3' noncoding region of the tml gene of the same virus. Recombinant plasmids were analyzed by restriction digest, and one which contained the PR-Q cDNA in the orientation appropriate for the production of a translatable PR-Q-encoding message, pCIB 1022, was chosen for further constructions.

A DNA fragment containing the double CaMV promoter, PR-Q cDNA, and tml 3' region was excised from pCIB1022 by digesting it with Xba I. It was inserted into the XbaI site of the plasmid pCGN1540. The binary transfer vector pCGN1540 contains a gentamycin resistance gene for selection in both *E. coli* and *Agrobacterium tumefaciens*, and pBR322 and PRiHRI origins of replication. Insertion into the Xba I site places the PR-Q expression cassette between DNA sequences corresponding to the right and left borders of the Agrobacterium T-DNA, along with a cassette for expression of the Tn5 neomycin phosphotransferase gene under the control of the mannopine synthase promoter and bounded by the 3' non-coding region of the mannopine synthase gene, and an *E. coli* lacZ gene for color production. The structure of the new plasmid, pCGN17991C, was shown by restriction analysis to be the one in which the mas promoter and the double CaMV promoter would intiate transcription in the same direction on the DNA template.

5. Transformation of Tobacco

Plasmid pCGN1791C was transformed into *A. tumefaciens* strain LBA4404. Transformation of *Nicotiana tabacum* cv. Xanthi.nc was by co-cultivation of the bacteria with leaf disks by standard methods. Transformed plant tissue was selected by resistance to kanamycin, and was regenerated to intact plants (T1 plants) by standard methods. About twenty plants were regenerated, starting with tissue which arose from independent transformation events.

6. Production and Biochemical Characterization of Homozygous Plants

Small samples of leaf tissue were taken from each of the T1 plants and denatured extracts from total leaf tissue were analyzed by SDS gels and Western blots, using antisera raised against PR-Q protein. The material from the transgenic plants which reacted with the antibody was compared to that which came from TMV-treated, untransformed tobacco, to material from untreated, untransformed tobacco, and to purified PR-Q protein on the same blot. Transgenic plants which did not contain a significant amount of immunoreactive material which was the correct molecular weight were discarded. The plants which were positive in this test were grown in a greenhouse until the flowering stage, and then they were individually bagged to ensure that only self-fertilization took place. The resulting seeds (T2 generation) were harvested, and 100 from each T1 plant were scored for resistance to kanamycin by germinating them on antibiotic-containing medium. Plants which gave seeds exhibiting approximately a 3:1 ratio of kanamycin resistance to sevsitivity were judged to contain a single locus of T-DNA insertion, and 8-10 offspring from each of these plants were grown to the flowering stage and bagged. During the growth of these plants, leaf samples were taken and analyzed for constitutive PR-Q expression as described. Based on these analyses, a lineage from one independent transformant was chosen as the one which accumulates the largest amount of PR-Q (1791C-18). Seeds from the individual T2 plants of this lineage were harvested and 100 were scored for kanamycin resistance. The complete absence of kanamycin sensitive seeds in this assay indicated that the seeds were derived from a parent homozygous for the trans gene. Seed lot 1791C-18-2 was homozygous by this criterion, and was used for testing against pathogens.

7. Test For Resistance To Cercospora nicotianae

Inoculum from *C. nicotianae* (ATCC strain 18366) was made by culturing a conidial suspension on CDV8 plates covered with sterile filter paper under black lights at 18 degrees Celcius for two weeks. The spores were collected by brushing the filter paper in distilled water, and the spore concentration was adjusted to 100,000-150,000 spores per ml. The suspension was sprayed onto the upper surface of the leaves of 8-week-old tobacco plants, which were then kept covered for 5-6 days by a plastic sheet to maintain high humidity. After that, the plants were kept moist by periodic spraying by an automatic system. The symptoms appeared 8-10 days later, and disease scores were obtained by recording the percent of leaf area infected by the fungus. The lesion mimic plants, 1791C-18-2, were significantly less infected than untransformed Xanthi.nc plants.

D. Constitutive Immunity (cim) Mutants in Arabidopsis

Considerable data shows a tight correlation between the expression of SAR genes and systemic acquired resistance (Ward et al. (1991) *Plant Cell* 3, 1085-1094, herein incorporated by reference; Uknes et al. (1992) *Plant Cell* 4, 645-656, herein incorporated by reference; Alexander et al. (1993) *Proc. Natl. Acad. Sci. USA* 90, 7327-7331, herein incorporated by reference; and Uknes et al. (1993) *Mol. Plant Microbe Interact.* 6, 680-685, herein incorporated by reference). In Arabidopsis, examples of well characterized SAR genes are PR-1, PR-2 and PR-5, with PR-1 expressed at the highest level with the lowest background. A high-throughput Northern blot screen was developed to identify Arabidopsis mutants that would have high concentrations of PR-1 mRNA during normal growth, with the idea that these mutants also express systemic acquired resistance. A number of mutants have been isolated using this screen and they have been shown to accumulate not only PR-1 but also PR-2 and PR-5 mRNAs (Lawton et al. (1993) *Mechanisms of Defense Responses in Plants* (Fritig, B. and Legrand, M., eds.) Dordrecht: Kluwer Academic Publishers, pp. 410-420, herein incorporated by reference; Dietrich et al. (1994) *Cell* 77, 565-577, herein incorporated by reference; and Weymann et al. (1995) *Plant Cell* 7, 2013-2022, herein incorporated by reference). The mutants also had elevated levels of SA and were resistant to pathogen infection, confirming that this approach can be used to isolate SAR signal transduction mutants.

Two classes of SAR signal transduction mutants were isolated using this screen. One class has been designated as lsd mutants (lsd=Lesion Simulating Disease). This class of mutants is referred to supra as "cim Class I" in Experimental Section "A", entitled "*Arabidopsis Lesion Mimic Mutants.*" Likewise, the cim1 mutant line described therein has more recently been renamed lsd2. This lsd class (aka cim Class I) formed spontaneous lesions on the leaves, accumulated elevated concentrations of SA, high levels of PR-1, PR-2 and PR-5 mRNA and was resistant to fungal and bacterial pathogens (Dietrich et al., 1994, supra; Weymann et al., 1995, supra).

The second class, called cim (cim=Constitutive IMmunity), is described below and has all the characteristics of the lsd mutants except spontaneous lesions. This second class (cim). corresponds to the "cim Class II" mutants discussed supra in Experimental Section "A". The cim3 mutant line described herein falls into this cim class (aka cim Class II) and is a dominant mutation with wild-type appearance that expresses stable, elevated levels of SA, PR-1 mRNA and disease resistance.

1. Isolation and Characterization of cim3 Mutants with Constitutive SAR Gene Expression - Experimental Procedures a. cim3 Mutant Isolation 1100 individual M2 mutagenized (EMS) Arabidopsis plants were grown in Aracon trays (Lehle Seeds, Round Rock, Tex.) in sets of approximately 100. Plants were grown as described in Uknes et al., 1993, supra, with special attention given to avoid over-watering and pathogen infection. Briefly, Metro Mix 360 was saturated with water and autoclaved three times for 70 minutes in 10 liter batches. The potting mix was stirred thoroughly in between each autoclaving. Seeds were surface sterilized in 20% Clorox for 5 minutes and washed with seven changes of sterile water before sowing. Planted seeds were vernalized for 3–4 days followed by growth in chambers with a 9 hour day and 15 hour night at 22_C. When the plants were three- to four-weeks-old, one or two leaves, weighing 50 to 100 mg, were harvested and total RNA was isolated using a rapid, mini-RNA preparation (Verwoerd et al. (1989) *Nuc. Acid Res.* 17, 2362). PR-1 gene expression was analyzed by Northern blot analysis (Lagrimini et al. (1987) *Proc. Natl. Acad. Sci. USA* 84, 7542–7546; Ward et al., 1991). Each set of plants also contained a non-treated *A. thaliana* Col-O and a 2-day INA-treated control. 80 putative mutants were isolated and progeny testing was performed on M3 plants. Approximately 20 M2 plants gave rise to M3 plants with increased PR-1 gene expression. All plants were maintained as described in Weymann et al., (1995), supra.

b. SA Analysis

Salicylic acid and its glucose conjugate were analyzed as described in Uknes et al., 1993, supra. Leaf tissue was harvested from 10 cim3 and 10 control, 4 week-old plants. Leaves from individual plants were harvested and analyzed for PR-1 gene expression. SA levels were measured from plants expressing PR-1.

c. Genetic Analysis

Back crosses to Columbia utilized the recessive glabrous trait as a marker for identification of F1 progeny. Col-gl1 flower buds were emasculated prior to pollen shed and pollen from the mutants was applied immediately and the following day. F1 plants were grown in soil and the out crossed plants were identified by the presence of trichomes.

For cim3, the original M2 plant identified in the screen and the M3 population appeared normal. However, as the cim3 plants were selfed some of the best expressing lines had low fertility. Following the back cross to Col-gl1, plants with normal appearance and fertility and strong PR-1 expression were obtained.

The thin, curled leaf phenotype characteristics of the initial isolate of cim3 was not evident in the F2 population, or subsequent selfed populations with PR-1 gene expression.

d. Crosses with NahG Arabidopsis

NahG plants were made by transformation of the 35S driven nahG gene into Arabidopsis using Agrobacterium mediated transformation. See, Huang, H. Ma, H. (1992) *Plant Mol. Biol. Rep.* 10, 372–383, herein incorporated by reference; Gaffney, et al. (1993) *Science* 261, 754–756, herein incorporated by reference; and Delaney, et al. (1994) *Science* 266, 1247–1250, herein incorporated by reference. Col-nahG Arabidopsis carries a dominant kanamycin resistance gene in addition to the dominant nahG gene, so Col-nahG was used as the pollen donor. F1 seed was hydrated in water for 30 minutes and then surface sterilized in 10% Clorox, 0.05% Tween 20 for five minutes and washed thoroughly in sterile water. Seeds were plated onto germination media (GM, Murashige and Skoog medium containing 10g/L sucrose buffered with 0.5 g/L 2-(N-morpholino) ethanesulfonic acid, pH 5.7 with KOH) containing 25 mg/ml kanamycin to select for $F_1$ plants. See Valvekens et al. (1988) *Proc. Natl. Acad. Sci., USA* 85, 5536–5540. Kanamycin resistant $F_1$ plants were transferred to soil after 18 days. The presence of the nahG gene and PR-1 expression was confirmed in all experiments by Northern blot analysis.

e. *Peronospora parasitica* Assays and Trypan-Blue Staining

*P. parasitica* (NoCo2) was maintained and inoculated as described in Uknes et al., 1992, supra. Plants were about 4 weeks old prior to inoculation. Trypan-blue staining was performed as described in Keogh et al. (1980) *Trans. Br. Mycol. Soc.* 74, 329–333; and in Koch and Slusarenko (1990) *Plant Cell* 2, 437–445.

f. *Pseudomonas syringae* Inoculation and Bacterial Growth Curves

Cultures of *Pseudomonas syringae* pv. tomato strain DC3000 were grown on King's B media (agar plates or liquid) plus rifampicin (50 µg/ml) at 28° C. (Walen et al. (1991) *Plant Cell* 3, 49–59). An overnight culture was diluted and resuspended in 10 mM $MgCl_2$ to a density of $2-5\times10^5$ cells per ml and injected into Arabidopsis leaves. Injections were carried out by creating a small hole with a 28 gauge needle midway up the leaf and then injecting approximately 250 µl of the diluted bacterial solution with a 1 cc syringe. At various time points, 10 random samples consisting of 3 random leaf punches from a #1 cork borer were taken from 10 plants from each treatment. The 3 leaf punches were placed in an eppendorf tube with 300 µl of 10 mM $MgCl_2$ and ground with a pestle. The resulting bacterial suspension was appropriately diluted and plated on King's B media plus rifampicin (50 µg/ml) and grown for 4 days at 28° C. Bacterial colonies were counted and the data were subjected to Student's t statistical analysis (Sokal and Rohlf (1981). Biometry. $2^{nd}$ ed. New York: W. H. Freeman and Company).

g. Chemical Induction of Systemic Acquired Resistance 2,6-Dichloroisonicotinic acid (INA) was suspended in sterile, distilled water as a 25% active ingredient formulated in a wetable powder (0.25 mg/ml, 325 µM; Kessmann et al. (1994) *Annu. Rev. Phytopathol.* 32, 439–59). All plants were sprayed with water or INA solutions to the point of imminent runoff.

Figure 5:
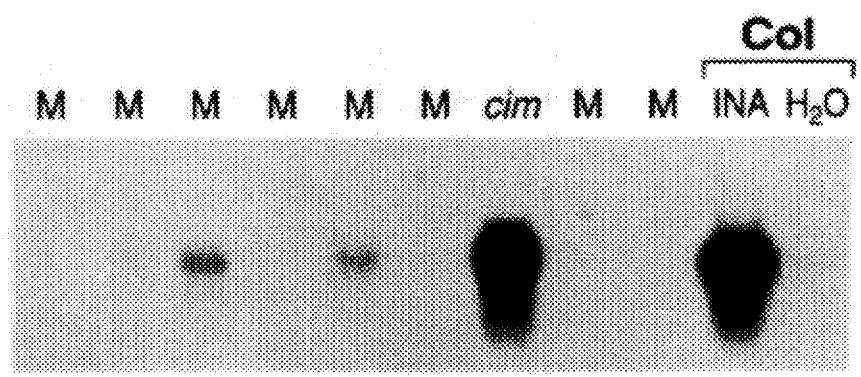
FIG. 5. Isolation of mutants based upon SAR gene expression. Leaves from individual plants were harvested and PR-1 gene expression was analyzed by RNA gel blot. M, different individual M2 Arabidopsis RNA samples; cim, putative cim mutant; Col, *A. thaliana* ecotype Columbia (Col-O). INA, Col-O treated with 0.25 mg/ml 2,6-dichloroisonicotinic acid (INA) 2 days before sampling. $H_2O$, Col-O treated with water.

2. Isolation and Characterization of cim3 Mutants with Constitutive SAR Gene Expression - Discussion of Results a. Isolation of Mutants with Constitutive SAR Gene Expression An RNA screen for PR-1 expression from leaves of EMS (M2) Arabidopsis plants grown under semi-sterile conditions was employed to isolate mutants in the SAR pathway. From 1100 mutagenized M2 plants, 80 putative mutants accumulating elevated levels of PR-1 mRNA were identified. Following progeny testing, five were chosen for further characterization. FIG. 5 shows the identification of a putative Arabidopsis mutant with elevated SAR gene expression in the absence of pathogen or inducing treatment. Progeny testing of the putative cim mutants confirmed that constitutive PR-1 expression was heritable. Of the cim mutants, two, cim2 and cim3, with the highest, most stable expression of PR-1 were characterized further.

Following crosses of cim2 and cim3 to ecotype Col-0 or La-er, a large proportion of F1 plants were identified with high SAR gene expression, suggesting these traits were dominant. In the case of cim2, some, but not all, F1 plants had constitutive SAR gene expression. Such a result would be expected if the cim2 mutant were dominant and carried as a heterozygote in the parent. Further genetic testing of cim2 showed continued variable segregation in the F2 generation, consistent with incomplete penetrance.

cim3 demonstrated a 1:1 segregation in the F1 generation whereupon two individual F1 plants expressing a high level of PR-1 mRNA were selfed to form an F2 population. F2 segregation, obtained by scoring PR-1 mRNA accumulation, showed 93 F2 plants with high PR-1 mRNA and 25 F2 plants without significant PR-1 mRNA accumulation giving a 3.7:1 ratio ($\chi^2=1.77$; $0.5>P>0.1$), which is consistent with the hypothesis that cim3 is a dominant, single gene mutation. Subsequent outcrosses confirmed that cim3 was inherited as a dominant mutation.

Figure 6:
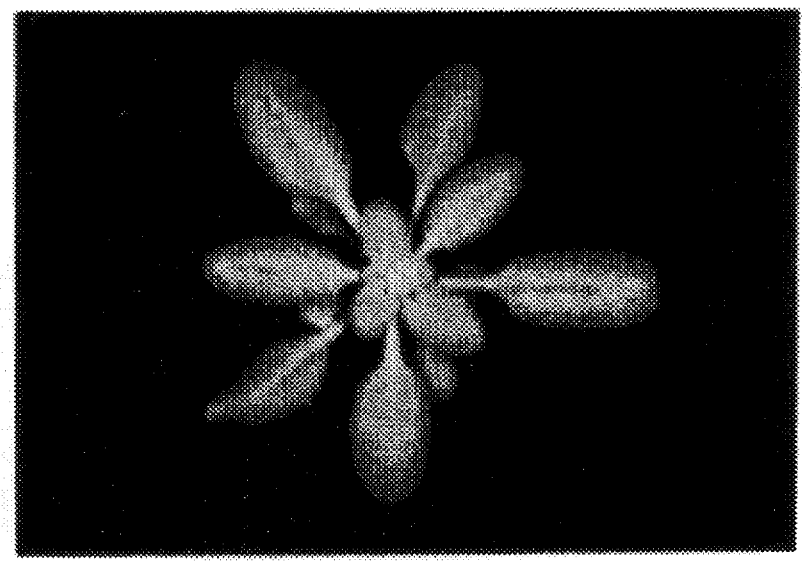
FIG. 6. cim3 mutant phenotype compared to wild-type. The mutant plant photographed was derived from a backcross to wild-type (Col-O). cim3 plants were confirmed by Northern blot analysis for PR-1 gene expression. The plants were photographed when approximately 4 weeks old.
Figure 6:
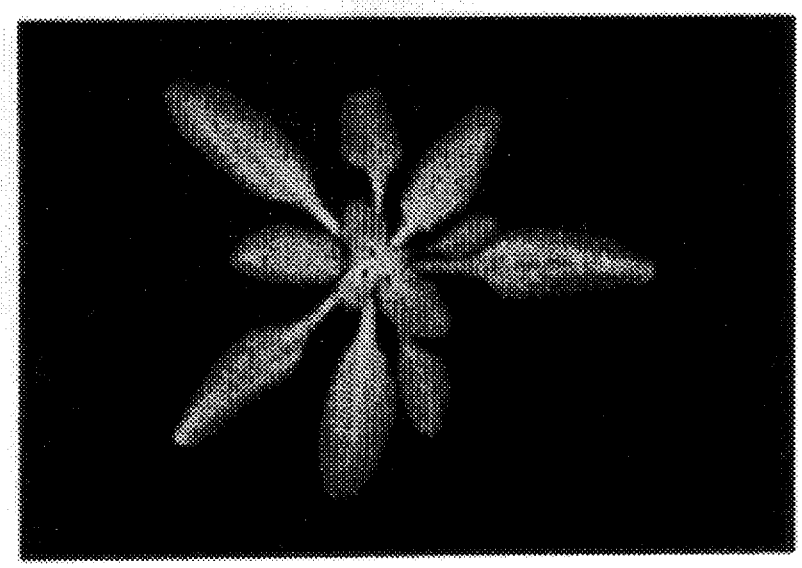

When initially identified, cim3 appeared slightly dwarfed with thin, distorted leaves. However, F2 plants resulting from a cross with ecotype Col-gl1 retained high SAR gene expression and could not be distinguished from wild-type plants (FIG. 6). This suggested that the dwarfed, distorted-leaf phenotype was caused by an independent mutation that was not associated with constitutive SAR gene expression. The cim3 mutant phenotype was also observed when plants were grown in sterile conditions confirming that PR-1 mRNA accumulation was not caused by a pathogen.

b. SAR Gene Expression in cim3

Figure 7:
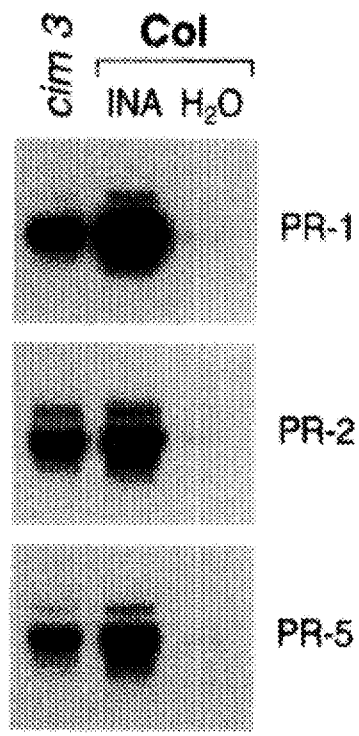
FIG. 7. Relative SAR gene expression in cim3. The cDNAs indicated were used to probe total RNA samples from the cim3 mutant, Arabidopsis ecotype Columbia (Col) and Columbia treated with 0.25 mg/ml INA for 2 days.

FIG. 7 shows that, in addition to PR-1, two other SAR genes, PR-2 and PR-5, are also highly expressed in cim3. Levels of SAR gene expression varied between the progeny, but were always more than 10-fold higher than the untreated control and similar to the levels obtained following a resistance-inducing INA treatment of wild-type plants.

c. SA Levels of cim3

Figure 8:
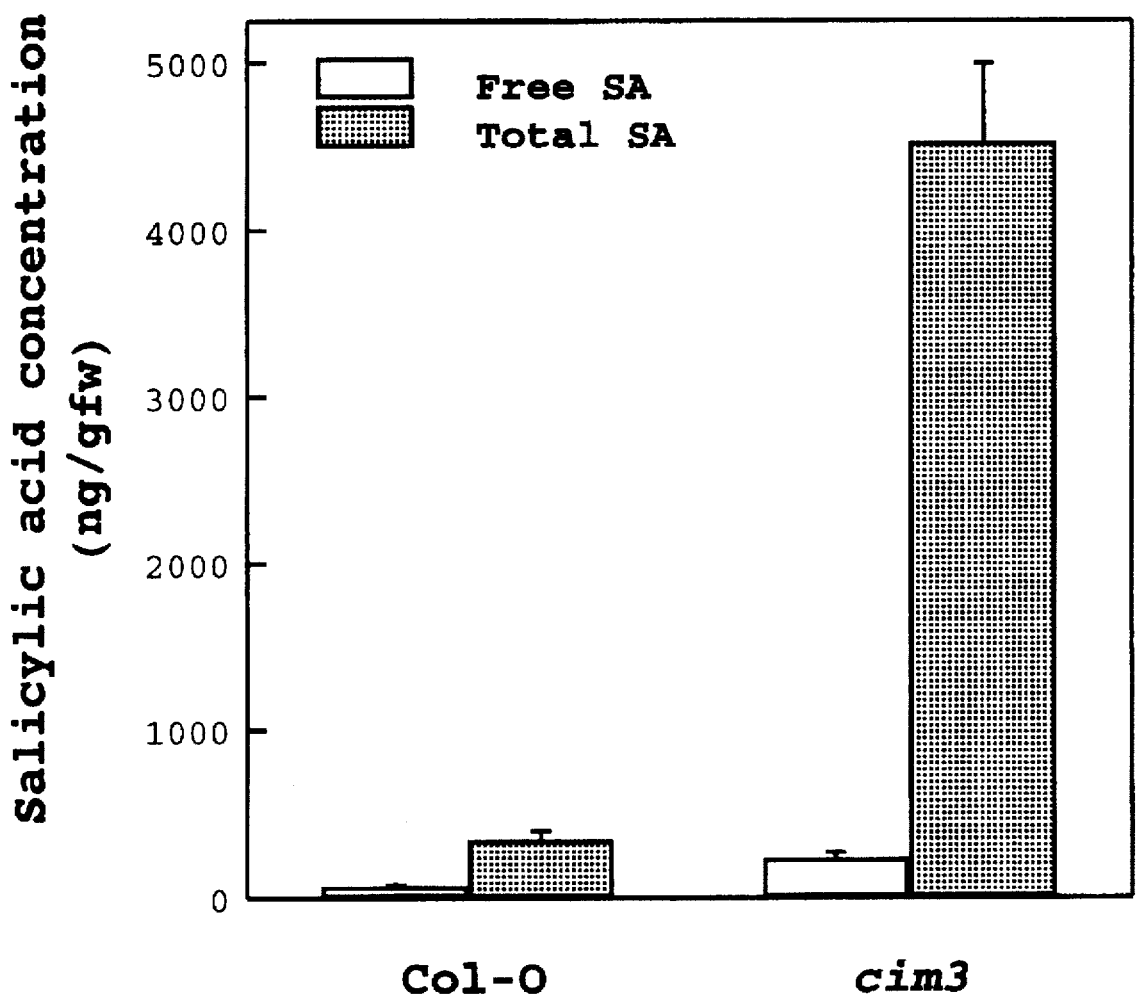
FIG. 8. Endogenous levels of SA and glucosylated SA in cim3 and wild type plants. The values represent the average of at least three replicates analyzed by HPLC from leaf tissue harvested from at least ten 4 week-old plants. cim3 plants were confirmed by Northern blot analysis indicating constitutive PR-1 gene expression.
Figure 9:
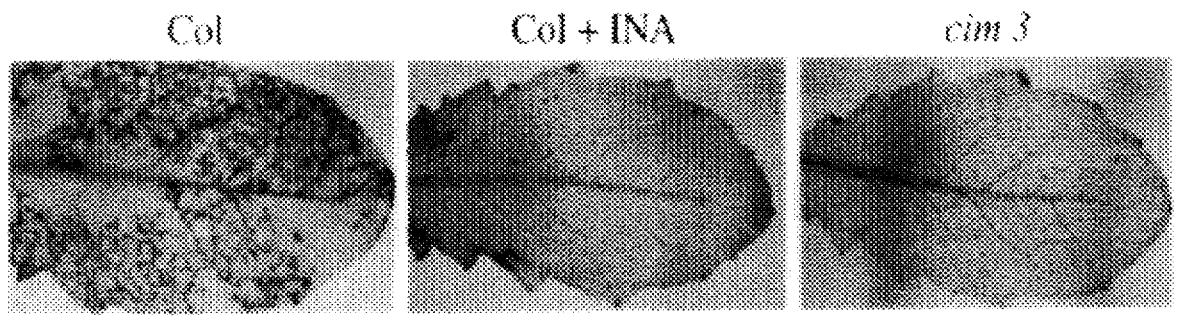
FIG. 9. Trypan-blue staining of cim3 Arabidopsis infected with *Peronospora parasitica* (NoCo2). The trypan-blue staining protocol allows visualization of dead cells and fungal structures 7 days after infection with *P. parasitica* (NoCo2). Col-O plants show extensive fungal infection while Col-O induced with INA and cim3 show no significant *P. parasiyica* growth or sporulation. Col-O. *A. thaliana* ecotype Columbia. INA. *A. thaliana* ecotype Columbia treated with 0.25 mg/ml 2,6-dichloroisonicotinic acid (INA) 2 days before sampling.

Endogenous concentrations of SA have been shown to increase following pathogen induced necrosis in Arabidopsis (Uknes et al., 1993, supra). FIG. 8 shows that the concentration of free SA in cim3 was 3.4-fold higher than in non-infected wild-type Arabidopsis (233±35 vs. 69±8 ng/g fresh weight, respectively). The glucose conjugate of SA (SAG) was 13.1-fold higher in cim3 than in non-infected wild-type Arabidopsis (4519±473 vs. 344±58 ng/g fresh weight, respectively). These increased levels of SA and SAG are comparable to the levels that have been reported for either pathogen-infected tissue or the cpr mutant.

d. Disease Resistance of cim3 cim3 was evaluated for resistance to *Peronospora parasitica* (NoCo2), the causal agent of downy mildew disease of Arabidopsis. Thirty cim3 (confirmed by PR-1 RNA expression) and thirty control plants (ecotype Columbia) were inoculated with *P. parasiyica*. Seven days later plants were analyzed for sporulation and stained with trypan blue to visualize fungal structures. FIG. 9 shows that wild-type (Col-0) plants support the growth of hyphae, conidia and oospores, which are stained with trypan-blue, while wild type plants treated with INA (0.25 mg/mL) and cim3 plants showed no fungal growth. The cim3-mediated resistance is typically seen as a small group of dead cells at the site of pathogen infection. This type of resistance is similar to that seen in Isd mutants (Dietrich et al., 1994, supra; Weymann et al., 1995, supra), or in wild-type plants in which SAR has been induced (Uknes et al., 1992, supra). Occasionally, intermediate resistance phenotypes were observed, including trailing necrosis in the wake of the hyphal tip in cim3 plants. This trailing necrosis is similar to that found in wild-type plants treated with low doses of SA or INA (Uknes et al., 1992, supra; Uknes et al., 1993, supra). However, sporulation was never observed on cim3 plants while all control plants showed sporulation. No spontaneous lesions were observed on uninoculated cim3 leaves when stained with trypan blue.

Figure 10A:
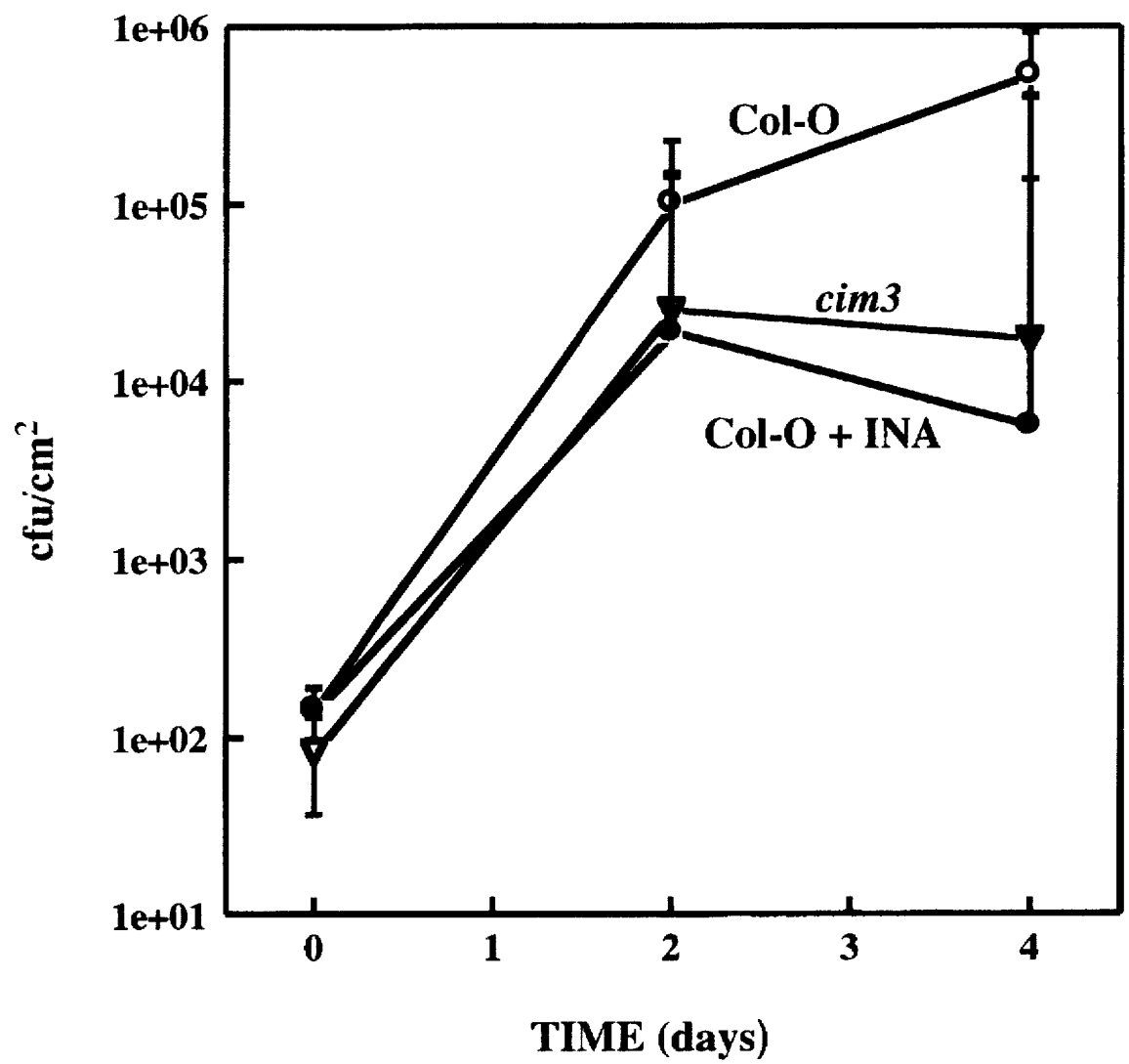
FIG. 10A. Growth of *Pseudomonas syringae* DC3000 in wild type and cim3 plants. Leaves of Arabidopsis plants were injected with a suspension of $2-5 \times 10^5$ bacterial cells/ml. Samples were taken 0, 2 and 4 days after injection. Data points represent the mean bacterial titer of 10 individual leaves per timepoint per genotype or treatment from the same experiment.
Figure 10B:
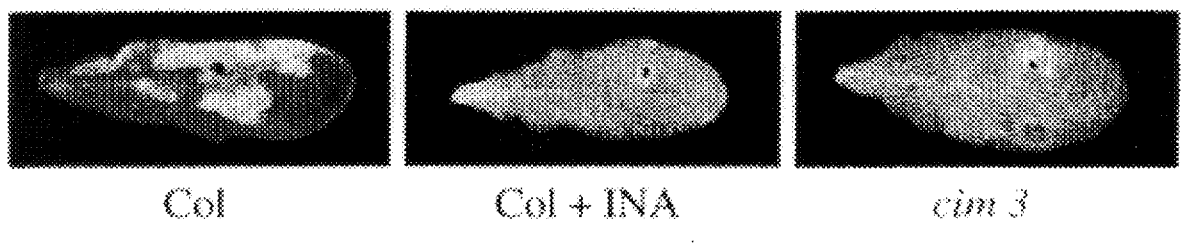
FIG. 10B. Growth of *Pseudomonas syringae* DC3000 in wild type and cim3 plants. Wild-type (Col-O), wild-type pretreated with INA, and cim3 leaves showing the extent of infection 4 days post-inoculation. Bacterial cells were injected into the upper half of the leaves as shown.

In addition to resistance to the fungal pathogen *P. Parasitica*, cim3 was also resistant to infection with the bacterial pathogen *Pseudomonas syringae* DC3000. Six-week-old wild-type (±INA treatment), and cim3 plants were inoculated with a suspension of *P. syringae* DC3000 and the progress of the disease was followed by monitoring the growth of the bacteria extracted from infected leaves over time (FIG. 10A). The difference in bacterial titers between Col-O, Col-O+INA and cim3 at either day 0 or day 2 was not statistically significant. However, by day four, there was a 31-fold decrease in bacterial growth between wild-type and cim3 plants ($P<0.003$; Sokal and Rohlf, 1981). The plants were also visually inspected for disease symptoms. Leaves from wild-type plants were severely chlorotic with disease symptoms spreading well beyond the initial zone of injection (FIG. 10B). In contrast, either wild-type plants pretreated with INA or cim3 plants were nearly devoid of disease symptoms.

e. The Role of SA in SAR Gene Expression and Disease Resistance in cim3

Figure 11:
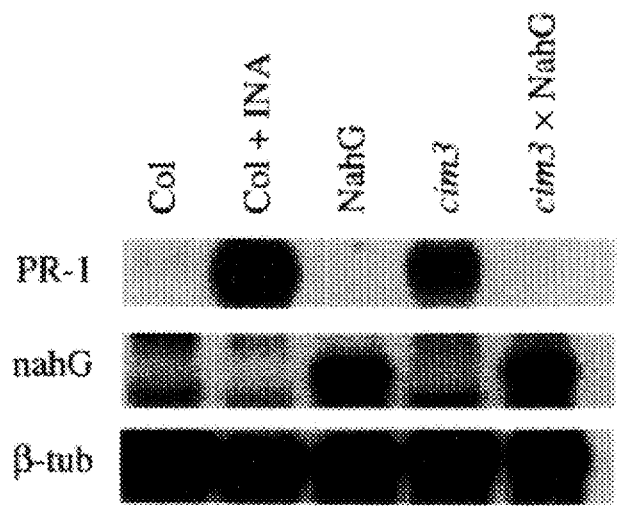
FIG. 11. mRNA expression in cim3 and cim3×nahG $F_1$ plants. PR-1 and nahG PCR-generated radiolabeled probes were used to identify their respective mRNA transcripts in a Northern blot analysis of wild-type Colombia (Col-O), Col plus 0.25 mg/ml INA, nahG, cim3, and $F_1$ progeny of cim3×nahG. β-tubulin (β-tub) was used as a loading control.

To investigate the relationship between SA, SAR gene expression and resistance in cim3, crosses were carried out with Arabidopsis plants expressing the salicylate hydroxylase (nahG) gene (Delaney et al., 1994). Because both the cim3 mutant and nahG phenotypes are dominant, epistasis between the two genes could be analyzed in F1 plants. Seventy F1 plants from a cim3 X nahG cross were analyzed for PR-1 and nahG gene expression. FIG. 11 shows that the presence of the nahG gene correlated with suppressed SAR gene expression. The presence of cim3 in each F1 was confirmed by assessing PR-1 mRNA in the resulting F2 segregants.

Figure 12:
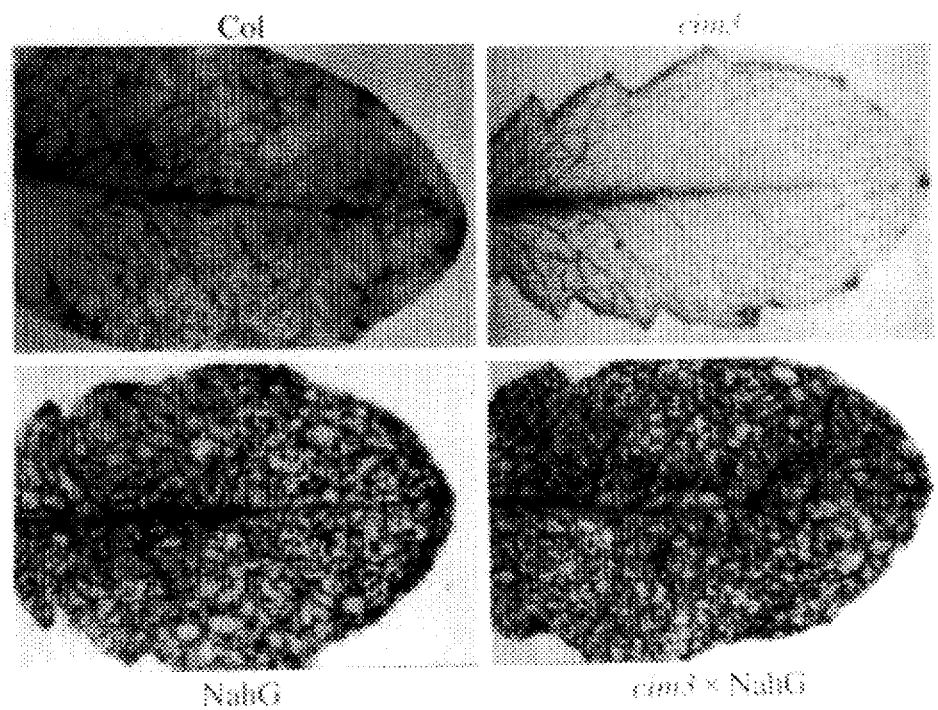
FIG. 12. Trypan blue staining cim3×nahG $F_1$ plants compared to wild-type and to the cim3 and nahG parents. Col-O plants exhibit moderate infection while the plants expressing nahG show extensive *P. parasiyica* (NoCo2) infection. cim3 shows no susceptability to *P. parasitica* (NoCo2). cim3×nahG plants show susceptibility symptoms similar to those seen in nahG plants. Tissue was stained and fixed 7 days post inoculation. The cim3 phenotype was verified by the presence of PR-1 mRNA in F2 segregants.

To determine if the cim3 mutation was epistatic to nahG with respect to disease resistance, 5 F1 plants from the cim3 X nahG cross, which had been confirmed for the presence of nahG and absence of PR-1 mRNA, were selfed and 20–30 F2 seed were planted. Expression of nahG and PR-1 mRNA was analyzed in individuals from this F2 population, which were then challanged with *P. Parasitica* (NoCo2) to assess their disease susceptibility. FIG. 12 shows cytological results from representative F2 segregants. Disease resistance conferred by cim3 was eliminated by the presence of the nahG gene, demonstrating that nahG is epistatic to cim3 for the SAR gene expression and disease resistance phenotypes.

E. Non-inducible Immunity (nim) Mutants

1. Use of nim Mutants in Disease Testing

Arabidopsis nim mutants are challenged with numerous pathogens and found to develop larger lesions more quickly than wild-type plants. This phenotype is referred to as UDS (i.e. universal disease susceptibility) and is a result of the mutants failing to express SAR genes to effect the plant defence against pathogens. The UDS phenotype of nim mutants renders them useful as control plants for the evaluation of disease symptoms in experimental lines in field pathogenesis tests where the natural resistance phenotype of so-called wild-type lines may vary (i.e. to different pathogens and different pathotypes of the same pathogen). Thus, in a field environment where natural infection by pathogens is being relied upon to assess the resistance of experimental lines, the incorporation into the experiment of nim mutant lines of the appropriate crop plant species would enable an assessment of the true level and spectrum of pathogen pressure, without the variation inherent in the use of non-experimental lines.

2. Assessment of the Utility of Transgenes for the Purposes of Disease Resistance nim mutants are used as host plants for the transformation of transgenes to facilitate their assessment for use in disease resistance. An Arabidopsis nim mutant line, characterized by its UDS phenotype, is used for subsequent transformations with candidate genes for disease resistance thus enabling an assessment of the contribution of an individual gene to resistance against the basal level of the UDS nim mutant plants.

3. nim Mutants as a Tool in Understanding Plant-Pathogen Interactions nim mutants are useful for the understanding of plant pathogen interactions, and in particular for the understanding of the processes utilized by the pathogen for the invasion of plant cells. This is so because nim mutants do not mount a systemic response to pathogen attack, and the unabated development of the pathogen is an ideal scenario in which to study its biological interaction with the host.

Of futher significance is the observation that a host nim mutant may be susceptible to pathogens not normally associated with that particular host, but instead associated with a different host. Arabidopsis nim mutants are characterized by the UDS phenotype. These plants are challenged with a number of pathogens that normally only infect tobacco, and found to be susceptible. Thus, the nim mutation causing the UDS phenotype leads to a modification of pathogen-range susceptibility and this has significant utility in the molecular, genetic and biochemical analysis of host-pathogen interaction.

4. nim Mutants for Use in Fungicide Screening nim mutants are particularly useful in the screening of new chemical compounds for fungicide activity. nim mutants selected in a particular host have considerable utility for the screening of fungicides using that host and pathogens of the host. The advantage lies in the UDS phenotype of the mutant that circumvents the problems encountered by the host being differentially susceptible to different pathogens and pathotypes, or even resistant to some pathogens or pathotypes. By way of example nim mutants in wheat could be effectively used to screen for fungicides to a wide range of wheat pathogens and pathotypes as the mutants would not mount a resistance response to the introduced pathogen and would not display differential resistance to different pathotypes that might otherwise require the use of multiple wheat lines, each adequately susceptible to a particular test pathogen. Wheat pathogens of particular interest include (but are not limited to) *Erisyphe graminis* (the causative agent of powdery mildew), *Rhizoctonia solani* (the causative agent of sharp eyespot), *Pseudocercosporella herpotrichoides* (the causative agent of eyespot), *Puccinia* spp. (the causative agents of rusts), and *Septoria nodorum*. Similarly, nim mutants of corn would be highly susceptible to corn pathogens and therefore useful in the screening for fungicides with activity against corn diseases.

nim mutants have further utility for the screening of a wide range of pathogens and pathotypes in a heterologous host i.e. in a host that may not normally be within the host species range of a particular pathogen and that may be particularly easily to manipulate (such as Arabidopsis). By virtue of its UDS phenotype the heterologous host is susceptible to pathogens of other plant species, including economically important crop plant species. Thus, by way of example, the same Arabidopsis nim mutant could be infected with a wheat pathogen such as *Erisyphe graminis* (the causative agent of powdery mildew) or a corn pathogen such as *Helminthosporium maydis* and used to test the efficacy of fungicide candidates. Such an approach has considerable improvements in efficiency over currently used procedures of screening individual crop plant species and different cultivars of species with different pathogens and pathotypes that may be differentially virulent on the different crop plant cultivars. Furthermore, the use of Arabidopsis has advantages because of its small size and the possibility of thereby undertaking more tests with limited resources of space.

F. Gene Cloning

The genes responsible for SAR gene expression and the lesion mimic trait in the different cim-type mutants and the nim mutant phenotype can be cloned and the corresponding cDNAs reintroduced into transgenic plants in either sense or antisense orientation to modify plant phenotype.

The cloning of the cim and nim mutation genes can be undertaken using techniques well known in the art. Markers that are located close to the mutation of interest can be identified using RFPL and RAPD technology. Typically this is done in a segregating population such as the F2 generation derived from a cross between a homozygous mutant and homozygous isogenic non-mutant, but alternatively it can be done in anther cultured dihaploid lines derived from a heterozygote individual. Once markers have been identified that co-segregate with the desired phenotype, the adjacent DNA can be cloned directly using the markers as probes in a genomic library screen coupled with subsequent "genome walking" to the desired destination. This step can be facilitated using YAC cloning techniques, which enable the subcloning of larger genomic fragments than is possible using traditional lambda phage or cosmid cloning techniques. The target sequence is precisely identified from its reintroduction from such a subclone into a host plant; depending on whether the mutant phenotype is dominant or negative, the reintroduction assay can be completed in the wild-type in primary transformants, or subsequent segregating generations. Having successfully cloned the mutant gene, the wild-type gene is easily clonable using the mutant gene as a probe in a library screen. "Map-based cloning technology", as it is known in the art, is well within the competence of one of ordinary skill in the art and is described, for example, in Arondel et al. (Science 258: 1353–1358 (1992)) and Martin et al. (Science 262: 1432–1436 (1993)).

As the inventors have established the existence and utility of the lesion mimic and nim mutations described in this specification, it will be apparent to those of ordinary skill in the art that the same types of mutation can be remade using insertion mutagenic techniques, which thus facilitate the subsequent cloning of the target gene of interest. Examples of insertion mutagenic techniques that are particularly useful in the context of cloning genes from plants include the T-DNA insertion technique in which the T-DNA from Agrobacterium is inserted randomly into the genome, and transposon insertion mutagenesis, where a natural or introduced transposon is induced to move to new locations throughout the genome. In each case the newly inserted DNA may disrupt a gene function and this may be assayable phenotypically. In the context of this invention, the phenotype assayed would be lesion mimic/SAR gene expression. As an alternative to assaying on the basis of SAR gene expression, it is possible to use a line transformed with a reporter gene such as luciferase under the regulation of an SAR gene promoter such as the PR-1a promoter as stock line in which to generate new mutants; cim mutants predictably express luciferase constitutively. The generation of T-DNA and transposon insertion mutant collections is a well documented technique in the literature and is well within the ordinary skill of the routineer (e.g. Feldman et al. Science 243: 1351–1354 (1989); Marks and Feldman Plant Cell 1: 1053–1050 (1989); Honma et al. Proc. Natl. Acad. Sci. USA 90: 6242–6246 (1993) and Aarts et al. Nature 363: 715–717 (1993)).

For genes that are tagged by T-DNA insertions, the wild-type uninterupted gene can be cloned by firstly cloning the T-DNA tagged gene, and then using sequences in the host genome that flank the T-DNA sequence as probes in the cloning of the wild-type gene. These techniques have been described by Feldman et al. (1989; Science 243: 1351–1354), Marks and Feldman (1989; Plant Cell 1: 1053–1050) and Hayashi et al. (Science 258: 1350–1352). For genes that are tagged by transposons, the wild-type uninterupted gene can be cloned using similar techniques and these have been described by Honma et al. (1993; Proc. Natl. Acad. Sci. USA 90: 6242–6246) and Aarts et al. (1993; Nature 363: 715–717).

An alternate approach to the cloning of genes tagged by insertion mutations is the use of subtraction techniques in which genomic DNA or cDNA derived from lines that are isogenic for all but the mutation are repeatedly hybridized to remove homologous sequences. This causes an enrichment for the sequences that differ between the two populations and that are subsequently subcloned and characterized. This technique and numerous variations thereof have been described extensively in the literature viz. Lamar and Palmer Cell 37: 171-? (1984); Kunkel et al. Proc. Natl. Acad. Sci. USA 82: 4778-? (1985); Nussbaum et al. Proc. Natl. Acad. Sci. USA 84: 6521-? (1987); Lisitsyn et al.; Science 259: 946–951 (1993).

Having cloned the wild-type gene from which the mutant phenotype derives, the cDNA corresponding to this wild type gene can be easily isolated using hybridization techniques that are well known in the art. Once isolated, the cDNA can be expressed in transgenic plant lines in sense orientation (to achieve overexpression of the gene) or in antisense orientation (to turn off the endogenous gene).

Expression in transgenic plants is achieved by the fusion of the cDNA identified and cloned as described above behind a suitable promoter in sense or antisense orientation. The cDNA is cloned into a plant expression casette behind a promoter expressed at high levels in transgenic plants and upstream of a transriptional terminator that is known to function in plants. A preferred promoter is the CaMV 35S promoter and a preferred terminator is the nopaline synthase terminator. The expression cassette is transferred to a binary vector (pCGN1540-Alexander et al., PNAS 90: 7327–7331 (1993) for Agrobacterium transformation and a direct gene transfer vector (pCIB3064; Koziel et al., Biotechnology 11: 194–200) for direct gene transfer. Agrobacterium is particularly suitable for the transformation of dicotyledonous species and direct gene transfer is particularly suitable for the transformation of monocotyledonous species. These techniques are well known in the art and are described in the two above-cited publications. Transgenic plants are screened for expression of sense or antisense RNA by Northern analysis and plants that express at high levels are selected for further phenotypic analysis.

Alternatively, promoters can be selected that have tissue specific expression pattern and would thus localize the effects of sense or antisense expression to particular cell types (for examples of such promoters see Edwards and Coruzzi, Ann. Rev. Genet. 24: 275–303 (1990)). Additionally promoters can be selected that are chemically regulatable and can thus be induced to express the transgene upon treatment of the transgenic plant with a specific chemical. A suitable promoter for this is the PR-1a promoter from tobacco (EP 0 332 104).

The expression of the cim and nim genes in transgenic plants in the appropriate host genotype background can be used to manipulate both disease resistance and/or host cell death. A transgene in sense or antisense, which may cause the host cell death phenotype (akin to the cell death apparent in the lesions of the lesion mimic mutants), can be expressed under the control of plant regulatory elements that are well known in the art to be expressed only in certain cell types (e.g. pollen or tapetal cells for the production of male sterility), or alternatively under the regulation of a chemically induced promoter (e.g. the PR-1a promoter). In one embodiment of the invention the transgene causing cell death (e.g. the cimI-derived gene in antisense) is expressed under a pollen specific promoter to cause male sterility in the female parent, whereas the pollinator carries a construct in antisense to the pollen specific construct (i.e. antisense-to-antisense), which is fused to the chemically regulatable PR-1a promoter. Thus, in the F1 hybrid plant population treatment with the chemical inducer of the PR-1a promoter will activate the pollinator-line derived gene and block the expression of the mother parent-derived gene allowing normal flowering of the F1 hybrid. In an analagous fashion, lines can be created that are female sterile (by utilizing a promoter that is expressed in gynaecium tissue only). From the biology of cim and nim mutants described in this specification, it is apparent that disease resistance phenotypes can be modified from the expression of antisense to cim or nim genes. In the case of cim genes, elevated disease resistance would be expected, whereas for nim genes a reduction in disease resistance would be expected.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for selecting, from a population of plants, plants that are resistant to viral, bacterial, or fungal pathogens and that constitutively express SAR genes, said method comprising:

a) evaluating the expression of SAR genes or resistance to viral, bacterial, or fungal pathogens in plants that have a lesion mimic phenotype; and b) selecting plants that are resistant to viral, bacterial, or fungal pathogens.

2. The method of claim 1, wherein said plants are selected based on expression of SAR genes.

3. The method of claim 1, wherein said plants are selected based on resistance to pathogens.

4. The method of claim 3, wherein said pathogen is a bacteria.

5. The method of claim 3, wherein said pathogen is a fungus.

6. The method of claim 1, wherein said plants are selected from corn, tomato, wheat, barley, tobacco, and sunflower.

7. The method of claim 6, wherein said plants are corn.

8. A method for breeding resistance to viral, bacterial, or fungal pathogens into plants, said method comprising:
   a) selecting lesion mimic phenotype mutants that constitutively express SAR genes;
   b) using said lesion mimic phenotype mutants in a breeding program; and
   c) selecting pathogen resistant progeny with desired phenotypic traits.

9. The method of claim 8, wherein said plants are selected from corn, tomato, wheat, barley, tobacco, and sunflower.

10. The method of claim 9, wherein said plants are corn.

11. The method of claim 8, wherein said pathogen is a bacteria.

12. The method of claim 8, wherein said pathogen is a fungus.

13. A method for breeding resistance to viral, bacterial, or fungal pathogens into plants, said method comprising:
   a) selecting lesion mimic phenotype mutants that are resistant to a viral, bacterial, or fungal pathogen and that constitutively express SAR genes;
   b) using said lesson mimic phenotype mutants in a breeding program; and
   c) selecting pathogen resistant progeny with desired phenotypic traits.

14. The method of claim 13, wherein said plants are selected from corn, tomato, wheat, barley, tobacco, and sunflower.

15. The method of claim 14, wherein said plants are coin.

16. The method of claim 13, wherein said pathogen is a bacteria.

17. The method of claim 13, wherein said pathogen is a fungus.

18. A method for selecting, from a population of Arabidopsis plants, non-inducible immunity (nim) mutant plants that are susceptible to viral, bacterial, or fungal pathogens and that are incapable of expressing SAR genes, said method comprising:
   a) evaluating the expression of SAR genes in plants that have a universal disease susceptibility (UDS) phenotype; and
   b) selecting plants that fail to express SAR genes upon infection by viral, bacterial, or fungal pathogens or upon treatment with a chemical inducer of SAR, and therefore fail to effect a defense against viral, bacterial, or fungal pathogens.

19. A method for screening chemical compounds for fungicidal activity, said method comprising:
   a) selecting an Arabidopsis nim mutant plant according to the method of claim 18;
   b) infecting said nim mutant plant with a fungal pathogen;
   c) treating said infected nim mutant plant with a chemical compound;
   d) assessing fungicidal activity of said chemical compound.

* * * * *

UNITED STATES PATENT AND TRADEMARK OFFICE
CERTIFICATE OF CORRECTION

PATENT NO   : 5,792,904
DATED:      : August 11, 1998
INVENTOR(S) : RYALS et al.

It is certified that there is an error in the above-identified patent and that said Letters Patent is hereby corrected as shown below:

On the title page, item [54] should read: -- METHOD FOR BREEDING DISEASE RESISTANCE INTO PLANTS --.

On the title page, item [75] Inventors should read: -- John A. Ryals, Cary; Scott J. Uknes, Apex, both of N.C.; Terrence Patrick Delaney, Ithaca, N.Y.; Eric R. Ward, Durham, N.C. --.

Signed and Sealed this

Third Day of April, 2001

Attest:

NICHOLAS P. GODICI

*Attesting Officer*        *Acting Director of the United States Patent and Trademark Office*